United States Patent [19]
McPherson

[11] Patent Number: 5,197,292
[45] Date of Patent: Mar. 30, 1993

[54] COOLING CAP FOR ATHLETES

[76] Inventor: Paul R. McPherson, 929 Middleton Ave., Lisle, Ill. 60532

[21] Appl. No.: 729,629

[22] Filed: Jul. 15, 1991

[51] Int. Cl.⁵ .............................................. F25D 23/12
[52] U.S. Cl. ...................................... 62/56; 62/259.3; 62/530; 128/402; 2/7
[58] Field of Search ...................... 62/259.3, 529, 530; 128/380, 402, 403, 399; 2/7

[56] References Cited

U.S. PATENT DOCUMENTS

| | | | |
|---|---|---|---|
| 340,793 | 4/1886 | Leonard | 2/7 |
| 1,567,931 | 12/1925 | Epler | 128/402 |
| 4,356,709 | 11/1982 | Alexander | 62/259.3 |
| 4,641,655 | 2/1987 | Abt | 62/259.3 |

*Primary Examiner*—John Sollecito
*Attorney, Agent, or Firm*—Patula & Associates

[57] ABSTRACT

A headwear device for cooling the wearer during athletic activity or work. The device is comprised of a cap having interior and exterior surfaces. At least one opening to at least one defined compartment chamber within the cap. The chamber is formed therewithin the interior and exterior surfaces of the cap. The chamber interior having at least one surface being of material capable of transmission of fluid from the chamber interior to the cap's interior surface.

21 Claims, 3 Drawing Sheets

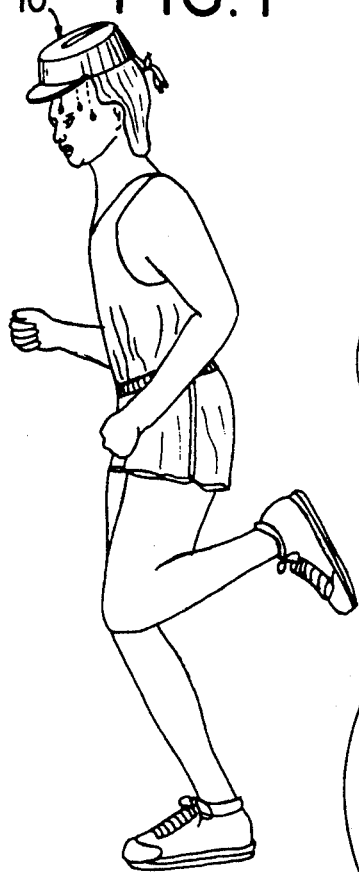
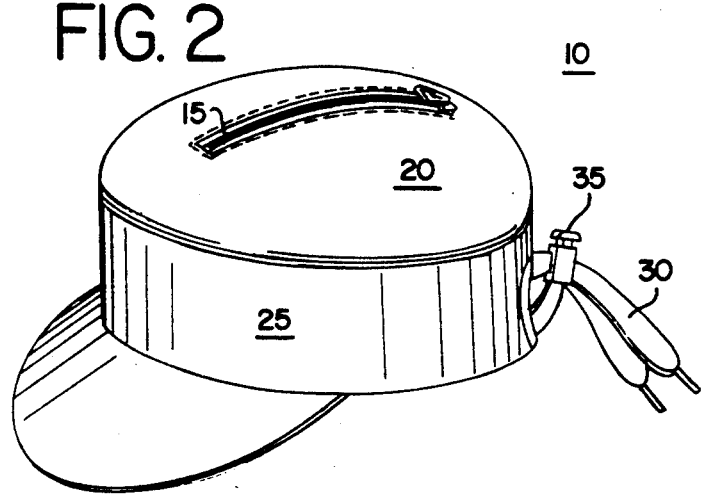
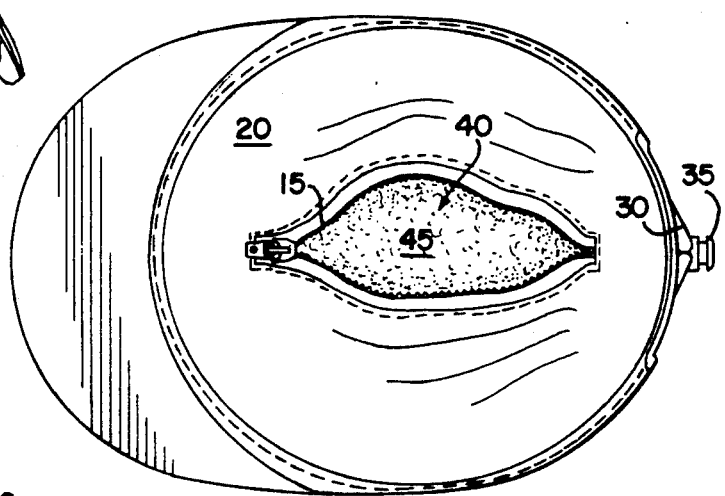
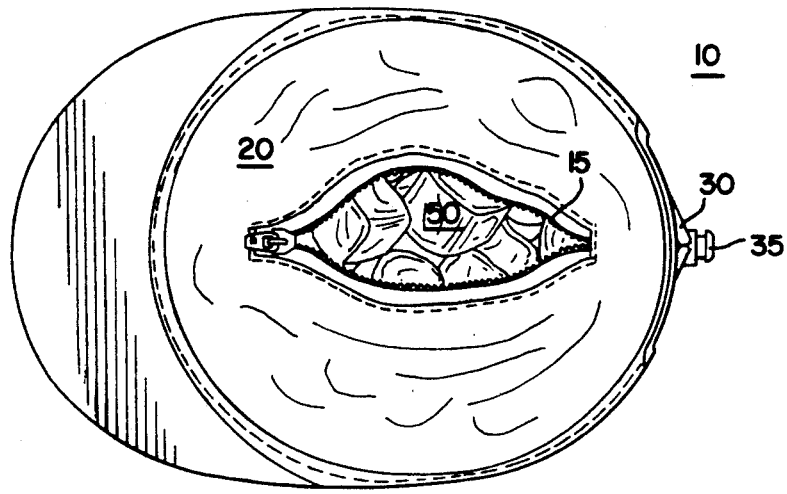

COOLING CAP FOR ATHLETES

This invention relates to a hat or cap with a provision to accept and retain ice which, upon the melting of the ice, cools the wearer's head.

BACKGROUND OF THE INVENTION

In the past many hat or caps had been developed to either include a container or bag for a coolant to be placed within in the hat or cap. For example, in U.S. Pat. No. 2,335,630 to Bachard, a double wall vacuum like container was filled with dry ice and arranged in a conducting structure to terminate behind the sweat band of the hat to keep the user's brow cool. This device differs from the present invention which allows readily available wet ice to melt onto the wearer's head instead of a complicated device relying on the evaporation of a specialized coolant that decomposes into a gas and then escapes.

U.S. Pat. No. 3,029,438 to Henscheo discloses a sponge strip which extends around the hat and is attached to a aluminum strip that is in contact with the head. It appears in theory that when the sponge strip is watersaturated, the water will begin to evaporate and causing a cooling effect as the heat is drawn away from the aluminum strip. The disadvantage with this system is that it requires a substantial amount of cooling from evaporating water and not the actual melting ice cubes placed upon the wearer's head as in the present invention.

U.S. Pat. No. 3,070,803 to Slepicka discloses a water reservoir bag which is improvious. In one form of the invention the top of the bag may have a filler plug made of sponge material in order for evaporation and thereby creating a cooling effect. The present invention is much more effective in the sense that it does not require an evaporative, but primarily allows melting ice water to seep directly on to the wearer's head, therefore providing superior cooling effect.

U.S. Pat. No. 4,172,495 to Zebuhr et al. is an elaborate arrangement with inlet and outlet manifolds formed into a shell-like hat or helmet surrounding the wearer's skull. On the melting of a frozen slurry, a hose connected to a slurry generator may be used to recharge the tube-like arrangement. Once recharged, the hoses are disconnected and the wearer can return to active endeavor. This device is vastly different from the present invention which is quite simple and economical and does not require use of a specialized fluid such as slurry and pumps and generators to perform an effective cooling of the wearer's head.

U.S. Pat. No. 4,356,709 to Alexander involves a doubled wall ice ca in which a cavity is provided for a sealed bag and placed on the head for cooling. The device provides a local application of ice as a source of cooling for the specific use for patients undergoing chemotherapy treatment. This device differs from the present invention in that no melted ice water travels to the user's scalp readily providing a effective cooling.

No known device allows for a simple positioning and use of readily available wet ice cubes to be placed within headgear apparel to provide superior and yet effective cooling of the wearer's head through the actual melting of the ice directly onto the wearer's scalp during athletic endeavors or other activities needing head cooling.

BRIEF SUMMARY OF THE INVENTION

The present invention involves a headgear device or cap with an upper chamber accessible from the top by zipper or other conventional closure. The bottom of the interior chamber is made of a sponge-like soft pliable material which supports the ice to prevent the ice from sitting directly on the wearer's scalp. This sponge like material also absorbs the melted ice and provides a moderating effect in the amount of melted ice applied to the wearer's scalp. A gauze or mesh-like additional layer is positioned beneath the sponge which provides strength and further support for the soft pliable material upon the weight of ice when positioned into the chamber. No known reference provides for melted ice water to travel to the scalp through the soft pliable layer and the resulting gauze or mesh-like material beneath. Further objects and advantages will become apparent in the following specification when considered in light of the attached drawings.

Numerous other advantages and features of the invention will become readily apparent from the detailed description of the preferred embodiment of the invention, from the claims, and from the accompanying drawings, in which like numerals are employed to designate like parts throughout the same.

BRIEF DESCRIPTION OF THE DRAWINGS

A fuller understanding of the foregoing may be had by reference to the accompanying drawings, wherein:

FIG. 1 is a perspective view of the present invention as utilized in a typical athletic endeavor such as running;

FIG. 2 is a side perspective view of the present invention;

FIG. 3 is a top plan view of the present invention;

FIG. 4 is a top plan view of the present invention with ice cubes inserted therein;

DESCRIPTION OF THE PREFERRED EMBODIMENT

Figure 5:
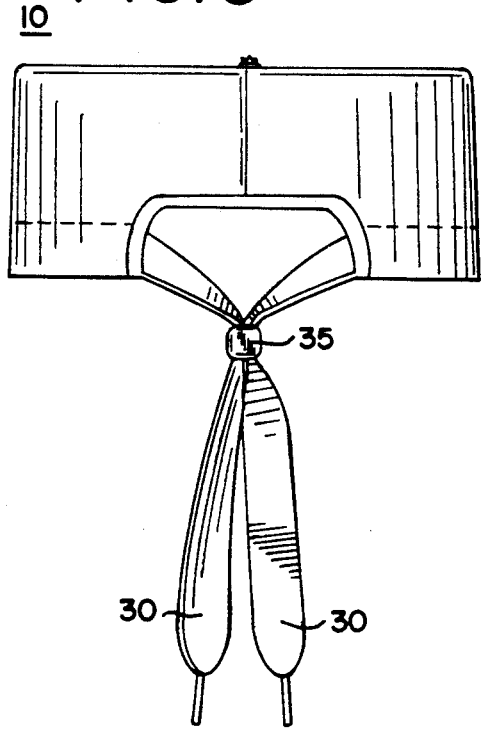
FIG. 5 is a rear elevational view of the present invention.

While the invention is susceptible of embodiment in many different forms there is shown in the drawings and will be described herein in detail, a preferred embodiment of the invention. It should be understood, however, that the present disclosure is to be considered an exemplification of the principles of the invention and is not intended to limit the spirit and scope of the invention and/or claims of the embodiment illustrated.

FIG. 1 is a perspective view of the preferred embodiment of the present invention 10 as utilized in a typical athletic endeavor such as running. The invention 10 is worn conventionally atop the wearer's head as shown.

FIG. 2 is a side perspective of the preferred embodiment of the present invention 10 showing the compartment closure device such as a zipper 15 or other closure means affixed with the upper surface 20. A side wall 25 of the invention 10 supports the upper surface 20 and has a gathering or fastening means such as a cord 30 positioned therewith. A clamping means 35 is positioned on said cord 30 to lock the cord 30 at the desired tightness around the wearer's head. The fastening means of cord 30 and clamping means 35 can also be seen in FIG. 5.

FIG. 3 is a top plan view of the present invention in which a cavity or compartment 40 is depicted by the opening or unfastening of zipper 15. At the base of compartment 40, a foam rubber or sponge-like soft pliable material 45 supports the ice 50 (as shown in FIG. 4) from sitting directly on the wearer's scalp. This material 45 may be absorbent or not, as desired, as it helps prevent the uncomfortable effect of sharp ice edge points confronting the wearer's scalp. Material 45 also acts as a physical barrier to prevent direct application of ice 50 unto the wearer's scalp and to moderate the rate of melted ice water from running down the wearer's head.

Figure 6:
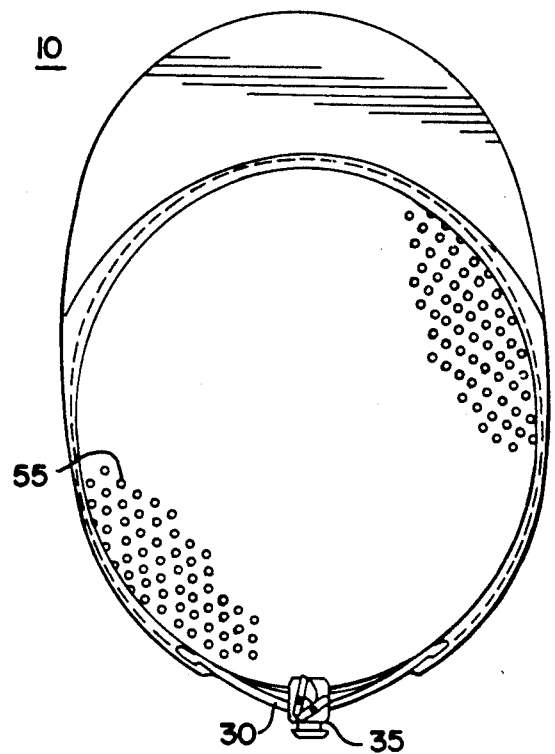
FIG. 6 is a bottom plan view of the present invention.

FIG. 6 is a bottom view of the invention 10, depicting the gauze or mesh-like material 55 which is used to provide further structural support for the soft pliable material 45 which is directly above the mesh-like material 55. Both soft pliable material 45 and mesh-like material 55 are to the nature to allow the melting ice in the form of water, pass through the same to the wearer's scalp and head.

Figure 7:
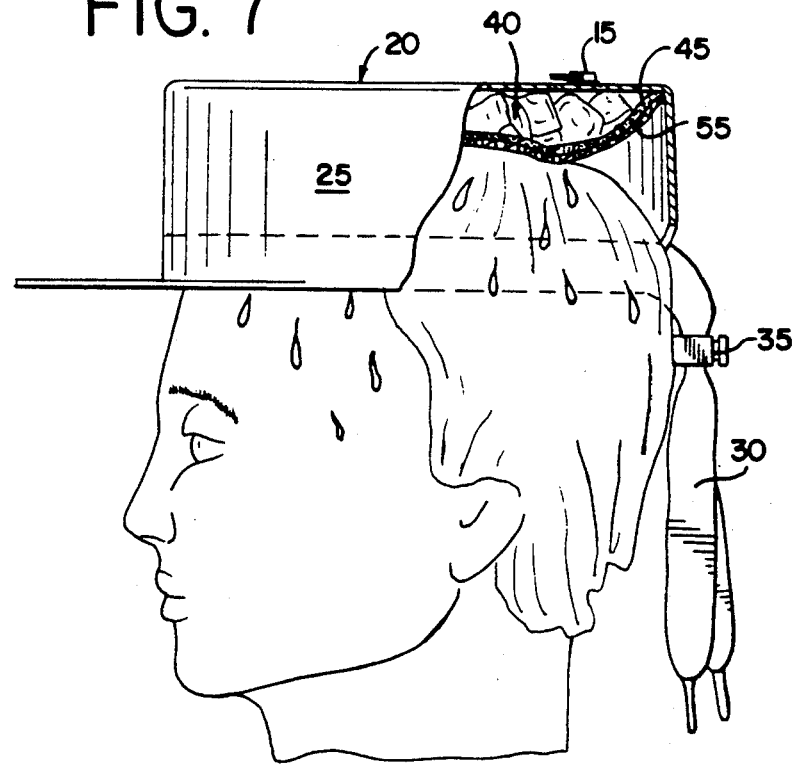
FIG. 7 is a side elevational view with partial cut out as applied onto a wearer's head.

FIG. 7 depicts in partial cross-section, the invention 10 in actual use. Specifically, the insertion of ice 50 into compartment 40 and closure thereof by zipper 15 or other conventional closure means. The ice 50 is supported by soft pliable material 45 and mesh-like material 55 such that the ice, as it melts, passes a liquid onto the wearer's head to provide cooling. Cord 30 is comfortably brought-up close to the desired head hugging snuggness by the use of clamping means 35.

Figure 8:
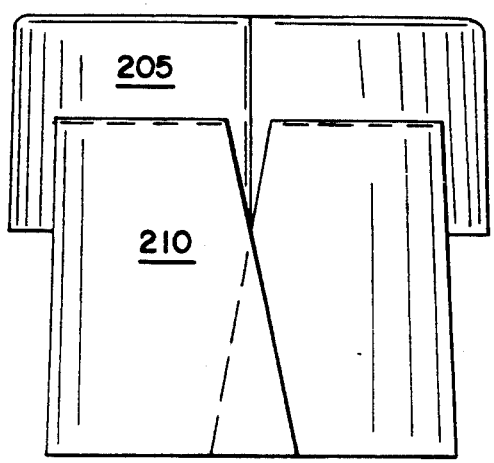
FIG. 8 is a rear elevational view of an alternative embodiment of the present invention.
Figure 9:
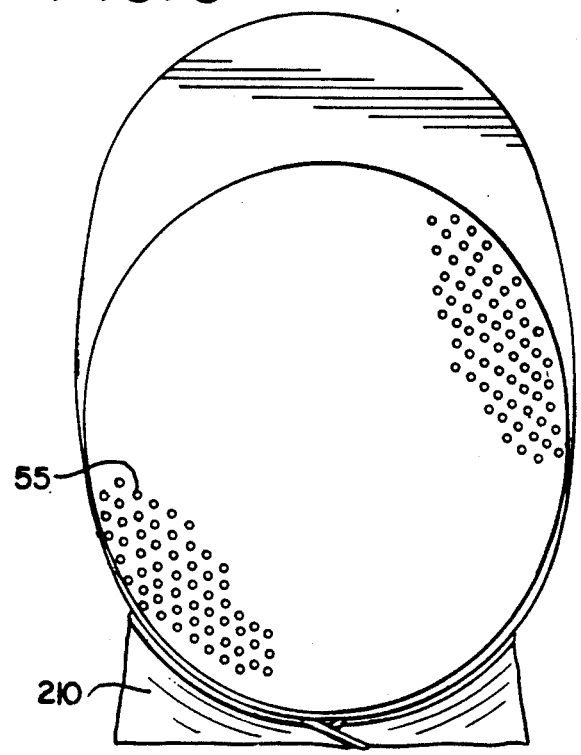
FIG. 9 is a bottom plan view of an alternative embodiment of the present invention.
Figure 10:
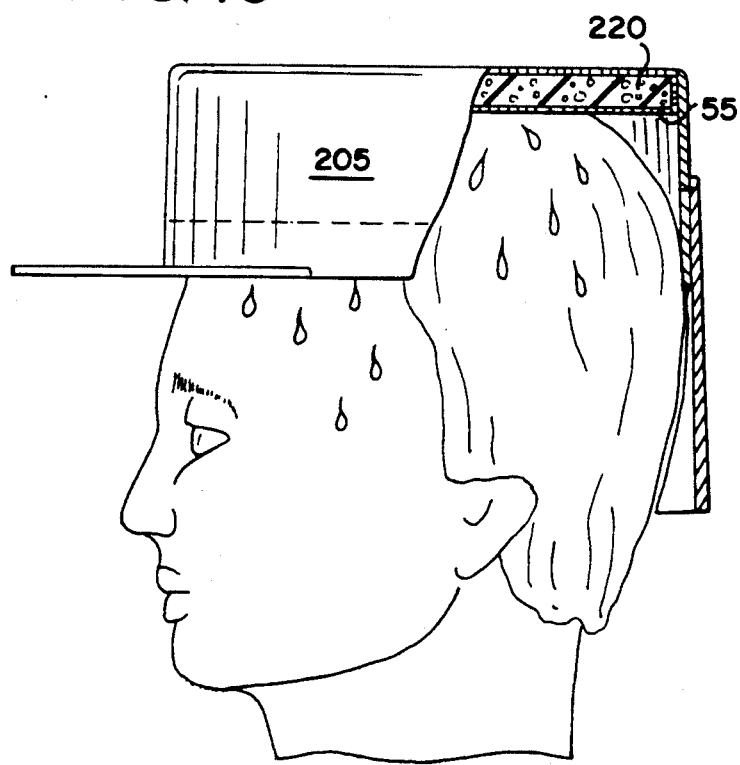
FIG. 10 is a side with cross-sectional view of the present invention as applied to a wearer's head.

Shown in FIGS. 8-10, is an alternative embodiment of the present invention 200. The invention 200 is similar to the invention described and shown in the preferred invention except that no access chamber is envisioned like the preferred embodiment. Instead a fluid absorbing material is contained between the exterior and interior of the cap. Sidewalls 205 have a set of back flaps 210 which hang down the rear of the invention 200 as shown in FIG. 8.

In FIG. 9 there is a depicted a gauze or mesh-like material 55 like that shown and described in the preferred embodiment.

In FIG. 10 the alternative embodiment is depicted in partial cross-section, the invention 10 positioned on a wearer's head such that an absorbent foam rubber or other sponge-like material 220 is supported inside the invention 10 by a rigid or semi-rigid mesh or gauze like material 55 such that the user moistens the internal section of the invention 10 with cool or cold water or other liquid 220 to be absorbed and retained therein, to again slowly drip, by the force of gravity, onto the wearer's head during use. Alternatively, the sponge-like fluid retaining material may be saturated and frozen before use to last a longer period of time as the wearer utilizes the invention 10 in warm weather or wherever substantial cooling is necessary The foregoing specification describes only the preferred and alternative embodiments of the invention as shown. Other embodiments besides the ones depicted and described may be articulated as well. The terms and expressions therefore serve only to describe the invention by example only and not to limit the invention. It is expected that others will perceive differences which while differing from the foregoing, do not depart from the spirit and scope of the invention herein described and claimed.

What is claimed is:

1. A headwear device for cooling the wearer, comprising:
   a cap having an interior surface and exterior surface, said cap having at least one opening to at least one defined compartment chamber within, said chamber formed therewithin by the interior surface of said cap and an exterior surface of said cap; and
   said chamber interior adapted to contain ice and having at least one surface comprising means for transmitting fluid melted ice from said chamber interior through said caps interior surface and dripping said fluid at a moderate rate onto the head of the wearer.

2. The headwear device of claim 1, wherein said chamber interior surface is further comprised of fluid absorbing material and rigid fabric means for supporting said absorbing material within said compartment interior.

3. The headwear device of claim 2, wherein said absorbing material is open cell foam.

4. The head wear device of claim 2, wherein said rigid fabric means is of a mesh configuration.

5. The head wear device of claim 1, further comprising a means for reusable closure of said at least one opening.

6. The head wear device of claim 5, wherein said closure means is a zipper.

7. The head wear device of claim 5, wherein said closure means is a hooks and loops type closure.

8. A headwear device for cooling a wearer by melting ice, comprising:
   a cap having an exterior surface and an interior surface, said interior surface is in proximity to the wearer's head;
   cooling compartment defined between and by said interior and exterior surfaces;
   said cooling compartment containing ice;
   access means for access to said compartment; and
   fluid support and transmission means disposed on said interior surface for draining fluid melted ice at a moderated rate to be conducted to the wearer's head, said fluid support and transmission means in fluid communication to cooling compartment of said interior surface of said cap, such that when the ice melts in said cooling compartment, the melted ice is transmitted through said fluid support and transmission means to the wearer's head.

9. The headwear device of claim 8, wherein said fluid support and transmission means is comprised of a rigid fabric means for supporting the ice.

10. The headwear device of claim 8, wherein said fluid support and transmission means is open cell foam.

11. The headwear device of claim 8, wherein said access means is positioned on said interior surface of said cap.

12. The headwear device of claim 8, wherein said access means is positioned on said exterior surface of said cap.

13. The headwear device of claim 8, further comprising a means for reusable closure of said access means.

14. The headwear device of claim 13, wherein said closure means is a zipper.

15. The headwear device of claim 13, wherein said closure means is a hoops and loops type closure.

16. The headwear device of claim 13, wherein said closure means is a complementary button and button hole type closure.

17. A headwear device for cooling a wearer by melting ice, comprising:
   a cap having an exterior surface and an interior surface, said interior surface is in proximity and conformity with the wearer's head;
   a cooling chamber adapted to accept and retain ice defined between and by said interior and exterior surfaces, defining a means to provide access to said chamber;
   reusable closure means for providing closure of said chamber access;
   open cell foam material affixed to the interior surface of said cap in fluid communication with said cooling chamber and the wearer's head; and
   semi-rigid mesh-like material in contact with and support of said open cell foam material said open cell foam material and said semi-rigid mesh-like material defining means for transmission of fluid melted ice onto the head of the wearer.

18. The headwear device of claim 17, wherein said reusable closure means is a zipper.

19. The headwear device of claim 17, wherein said reusable closure means is a hoops and loops type closure.

20. The headwear device of claim 17, wherein said reusable closure means is a complementary button and button hole type closure.

21. A method of cooling a wearer, using a cap having an interior surface and exterior surface, said cap having at least one opening to at least one defined compartment chamber within, said chamber formed therewithin by the interior surface of said cap and an exterior surface of said cap, said chamber further having an access and sad chamber interior having at least one means for transmitting fluid from said chamber interior through said caps interior surface onto the wearer, comparing the steps of:
   opening said access;
   depositing ice within the at least one defined compartment chamber;
   closing said access;
   allowing the ice to melt; and
   passing the melted ice through said at least one mean for transmitting fluid and dripping it onto the head of the wearer.

* * * * *